US006528795B2

(12) United States Patent
Kurfess et al.

(10) Patent No.: US 6,528,795 B2
(45) Date of Patent: Mar. 4, 2003

(54) COMPTON SCATTER IMAGING INSTRUMENT

(75) Inventors: James D. Kurfess, Gambrills, MD (US); Richard Kroeger, Bowie, MD (US); W. Neil Johnson, Alexandria, VA (US); Bernard Phlips, Accokeek, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 111 days.

(21) Appl. No.: 09/845,107

(22) Filed: Apr. 27, 2001

(65) Prior Publication Data

US 2002/0008205 A1 Jan. 24, 2002

Related U.S. Application Data

(60) Provisional application No. 60/200,015, filed on Apr. 27, 2000.

(51) Int. Cl.[7] ............................... G01T 1/24; G01T 1/164
(52) U.S. Cl. ............................... 250/370.1; 250/370.08; 250/370.13; 250/366; 250/369
(58) Field of Search ...................... 250/370.13, 370.09, 250/370.1, 366, 367, 369, 363.02

(56) References Cited

U.S. PATENT DOCUMENTS

| 4,857,737 | A | * | 8/1989 | Kamae et al. | ......... 250/363.02 |
|---|---|---|---|---|---|
| 5,175,434 | A | * | 12/1992 | Engdahl | ................. 250/363.02 |
| 5,506,408 | A | * | 4/1996 | Vickers et al. | ............... 250/366 |
| 5,567,944 | A | * | 10/1996 | Rohe et al. | ............. 250/363.03 |
| 5,665,971 | A | * | 9/1997 | Chen et al. | ............. 250/361 R |
| 5,821,541 | A | * | 10/1998 | Tumer | .................... 250/363.03 |
| 2001/0016029 | A1 | * | 8/2001 | Tumer | ....................... 378/98.8 |

FOREIGN PATENT DOCUMENTS

JP           01227050 A   *   9/1989   ........... G01N/23/06

OTHER PUBLICATIONS

Dogan, WEHE, Optimization and Angular Resolution Calculations for Multiple Compton Scatter Camera, Nuclear Science, Symposium and Medical Imaging Conference, Oct., 1993, IEEE Conference Record, pp 269–273.

Kurfess et al., Considerations for the Next Compton Telescope Mission, Fifth Compton Symposium—Sep. 1999, Portsmouth, New Hampshire, published in Proceedings from the Fifth Compton Symposium, 2000.

Kurfess, Prospects for a High Sensitivity Compton Telescope, Fifth Compton Symposium Sep. 1999, Portsmouth, New Hampshire, published in Proceedings from the Fifth Compton Symposium, 2000.

(List continued on next page.)

*Primary Examiner*—Constantine Hannaher
*Assistant Examiner*—Albert Gagliardi
(74) *Attorney, Agent, or Firm*—John J. Karasek; Lawrence G. Legg

(57) ABSTRACT

A device for determining the photon energy $E_1$ and direction cone angle of incident gamma ray includes a radiation detector for receiving an incident gamma ray having an unknown photon energy $E_1$ and an unknown direction and for scattering the gamma ray with two Compton scattering interactions and a subsequent scattering or absorption interaction. The detector provides three outputs, each output corresponding to one of the Compton scattering and the subsequent scattering or absorption interactions, to a processor, which is programmed to calculate the photon energy $E_1$ and direction cone angle of the incident gamma ray based on these outputs. The detector configuration, for example one that includes multiple detector layers, provides an accurate determination of both the position and energy of the incident gamma ray, while the calculation of the photon energy $E_1$ and direction cone angle of the incident gamma ray does not require absorption and measurement of the entire or substantially all the energy $E_1$ in the detector.

27 Claims, 8 Drawing Sheets

OTHER PUBLICATIONS

Inderhees et al., Spectroscopy, Imaging and Compton–scatter Polarimetry with a German Strip Detector, IEEE Transactions on Nuclear Science, vol. 43, No. 3, Jun. 1996, pp. 1467–1471.

Phlips et al., Performance of a Compton Telescope using Position–Sensitive Germanium Detectors, IEEE Transactions on Nuclear Science, vol. 43, No. 3, Jun. 1996, pp. 1472–1475.

Kroeger et al., Thin Scintallators and Position Sensitive Photomultiplier Tubes for Hard X–ray Imaging in Space, IEEE Transactions on Nuclear Science, vol. 44, No. 3, Jun. 1997, pp. 881–884.

Kurfess et al., Compton Scatter Imaging in Astrophysics, IEEE Transactions on Nuclear Science, vol. 45, No. 3, Jun. 1998, pp. 936–942.

Inderhees et al., Capacitive Charge Division Readout of a Double–sided Germanium Strip Detector, IEEE Transactions on Nuclear Science, vol. 42, No. 4, Aug. 1995, pp. 428–431.

Kroeger et al., Charge Sensitive Preamplifier and Pulse Shaper using CMOS process for Germanium Spectroscopy, IEEE Transactions on Nuclear Science, vol. 42, No. 4, Aug. 1995, pp. 921–924.

\* cited by examiner

COMPTON SCATTER IMAGING INSTRUMENT

The present application claims the benefit of the priority filing date of provisional patent application No. 60/200,015, filed Apr. 27, 2000.

BACKGROUND OF THE INVENTION

1. Field of the Invention

This invention relates to a method and devices using the method for measuring incident gamma-ray energy and direction. More particularly, the invention relates to measuring energy losses and positions of two Compton scatter interactions followed by a measurement of the position of a third Compton scatter or photoelectric interaction to determine the incident gamma-ray energy and direction cone without the necessity for absorbing the full energy of the incident gamma ray.

2. Description of the Related Art

Gamma ray imaging and detection is used in many scientific and commercial applications, including medical imaging, nuclear spectroscopy, and gamma ray astronomy.

One application that makes use of gamma ray imaging is gamma ray astronomy. In the conventional approach two position-sensitive detector arrays are used. The first array uses low-Z scintillation detectors and the second array, separated some distance from the first, uses high-Z scintillation detectors. Gamma rays incident on the first detector array undergo Compton scattering, and the Compton scattered gamma rays must be fully absorbed in the second detector array in order to estimate the energy and direction of the initial gamma ray. This approach has several limitations, including low efficiency, poor energy resolution and poor angular (imaging) resolution.

Alternative concepts to improve on these limitations have been proposed or undertaken that use detectors with improved position and/or energy resolution. However, in all of these approaches the fill energy of the initial gamma ray must be absorbed in order to determine the energy and direction of the incident gamma ray.

Another application is medical imaging using positron emission tomography (PET). In PET, a radio-pharmaceutical positron emitter is administered to a patient. In some PET applications, the radio-pharmaceutical is selected for its ability to preferentially concentrate in a desired tissue, e.g. a tumor. In other applications, the biological uptake or distribution of the radio-pharmaceutical is used to study organ function (e.g. brain or heart). In these applications, PET applies the mechanism whereby the positrons from the radio-pharmaceutical annihilate with electrons to create two annihilation gamma rays, each having an energy of 511 keV, that are emitted in opposite directions at an angle of almost exactly 180 degrees. The gamma rays are detected with position-sensitive detectors and the location of the detections determines a line on which the radioactive decay is located. Multiple events allow a more precise, 3-dimensional determination of the location of the concentration of radio-pharmaceutical and thus the location/morphology of the tumor or the function of the organ of interest. Typically, two identical detectors, each a combination of scintillators and photomultiplier tubes, are required for PET. This instrumentation, however, provides only moderate energy resolution and position resolution capabilities.

Another application is single photon emission computed tomography (SPECT). In SPECT, an injected radio-pharmaceutical emits a single gamma ray per radioactive decay. The direction of the emitted gamma ray is determined by using a collimator in conjunction with a position-sensitive scintillator-photomultiplier detector. The collimator only allows gamma rays from a single direction to reach the detector. This provides a two-dimensional view of the radioactivity. By moving the detector/collimator assembly to view the region-of-interest from many directions, or using multiple collimators and/or detectors, a three dimensional image can be reconstructed. The disadvantage of this technique is that the sharpest images are generated by collimators with narrow apertures. This is very inefficient and hence requires large doses or long collection times.

An application similar to SPECT is planar imaging, which is the traditional form of medical gamma ray imaging, in which a patient is injected with a radio-pharmaceutical as in SPECT but in which the collimator and detector are planar and are not rotated around the patient. The disadvantage is that the image generated is then a 2-dimensional projection rather than a 3-dimensional image of the radiation distribution.

In order to address the disadvantages of the current imaging systems, several concepts have been implemented or proposed that use the Compton scattering process. In Compton scattering, an initial gamma ray scatters off an electron in a position-sensitive detector and the Compton scattered gamma ray, reduced in energy, is detected by a second position-sensitive detector. The angle of scatter is determined from knowledge of the energy loss at the first and second detectors, where it is required that the full energy of the Compton scattered gamma ray is deposited in the second detector. With this information, the direction of the initial gamma ray is restricted to a cone whose axis is the line joining the two interaction sites and whose opening angle is twice the Compton scatter angle. This technique, for example, was the basis for a scintillation-detector imaging gamma ray instrument that was flown on a NASA mission to image the gamma ray sky. That instrument used low-Z and high-Z detectors for the first Compton scatter detector and the second full absorption detector, respectively. Significant disadvantages of this approach are poor detection efficiency and poor imaging resolution, the latter due to the poor energy resolution of the scintillation detectors.

Another proposed concept for an improved Compton imaging detector employs multiple Compton scattering in arrays of position-sensitive silicon detectors. In this approach, the initial gamma ray undergoes several Compton scatters in the silicon detector array, with the initial gamma ray energy either fully absorbed in the silicon array, or the gamma ray escaping the silicon array being absorbed in a scintillation detector surrounding the silicon array. Knowledge of the full energy loss is used, along with the energy losses and positions of the first two interactions to determine the Compton scatter angle at the first interaction site. The most probable interaction sequence for the Compton scatter events is determined from the consistency of the energy losses and scattering angles with the known physics of the Compton scattering process. An alternative to this technique recognizes that the full energy of the incident gamma ray need not be fully absorbed, and proposes that if the interaction order for four Compton scatters and the initial gamma-ray energy are unknown, the initial gamma ray energy and direction can still be deduced.

Another Compton imaging approach employs the use of position-sensitive gas or liquid detectors. A low-Z material (e.g. argon) is used for the Compton scatter detector while a high-Z material (e.g. xenon) is used to absorb the Compton scattered gamma ray. Disadvantages of this concept are the poor energy resolution of gas and liquid detectors relative to solid-state detectors, the low interaction efficiency in gas detectors compared to solid-state detectors, and the associated limitation to low-energy gamma-rays.

There is, therefore, a need for a gamma ray imaging device having improved imaging, improved detection efficiencies, better energy resolution, and capable of extending gamma-ray imaging capabilities to higher gamma-ray energies.

SUMMARY OF THE INVENTION

According to the invention, a device for determining the photon energy $E_1$ and direction cone angle of incident gamma ray with two Compton scattering interactions and one subsequent interaction includes a first radiation detector for receiving an incident gamma ray having an unknown photon energy $E_1$ and an unknown direction cone angle, for scattering a photon energy $E_2$ in a first Compton scattering interaction at a first scatter angle $\theta_1$, and for providing a first output corresponding to the first Compton scattering interaction; a second radiation detector for receiving photon energy $E_2$ and scattering some photon energy $E_3$ in a second Compton scattering interaction at a second scatter angle $\theta_2$, and for providing a second output corresponding to the second Compton scattering interaction; a third radiation detector for receiving photon energy $E_3$, and interacting with photon energy $E_3$ in a third interaction, and for providing a third output corresponding to the third interaction; and a processor for receiving and processing the first, second, and third outputs and for calculating the photon energy $E_1$ and direction cone angle of the incident gamma ray based on the outputs. The first, second, and third radiation detectors are sensitive to the position and energy of incident gamma ray, e.g. by virtue of being in a three-dimensional array providing a very accurate determination of the position of a scattering or other event. The device and processor include the capability to calculate the photon energy $E_1$ and direction cone angle of the incident gamma ray without the necessity for the absorption and measurement of the entire or substantially all of the energy $E_1$ in the detector. The detector also preferably includes the processor being programmed to reject a selected detection event, e.g. in an algorithm that also calculates the respective energy losses $L_1$, $L_2$, and $L_3$ in the first, second, and third radiation detectors.

The invention also includes a method for determining the photon energy $E_1$ and direction cone angle of incident gamma ray with two Compton scattering interactions and one subsequent interaction, comprising the steps of receiving an incident gamma ray having an unknown photon energy $E_1$ and an unknown direction cone angle, for scattering a photon energy $E_2$ in a first Compton scattering interaction at a first scatter angle $\theta_1$, and providing a first output corresponding to the first Compton scattering interaction; receiving photon energy $E_2$ and scattering some photon energy $E_3$ in a second Compton scattering interaction at a second scatter angle $\theta_2$, and providing a second output corresponding to the second Compton scattering interaction; receiving photon energy $E_3$, and interacting with photon energy $E_3$ in a third interaction, and providing a third output corresponding to the third interaction; and processing the first, second, and third outputs and calculating the photon energy $E_1$ and direction cone angle of the incident gamma ray based on the outputs, without necessarily absorbing and measuring the entire or substantially all of the energy $E_1$.

The invention provides substantially improved efficiency and imaging resolution compared to current systems.

The invention further provides a system that produces gamma-ray images having improved spectral resolution.

The invention is useful in military applications, for example for the location of fissile materials or for the location and identification of radioactive waste materials. The system and method also has non-military applications, for example in nuclear medical imaging and non-destructive testing, to name but a few.

The invention may have specific application in certain nuclear medical imaging applications, such as that described in pending U.S. patent application No. 09/854,467 filed on May 15, 2001, entitled "Coincident Multiple Compton Scatter Nuclear Medical Imager".

Additional features and advantages of the present invention will be set forth in, or be apparent from, the detailed description of preferred embodiments which follows.

DETAILED DESCRIPTION

Figure 1:
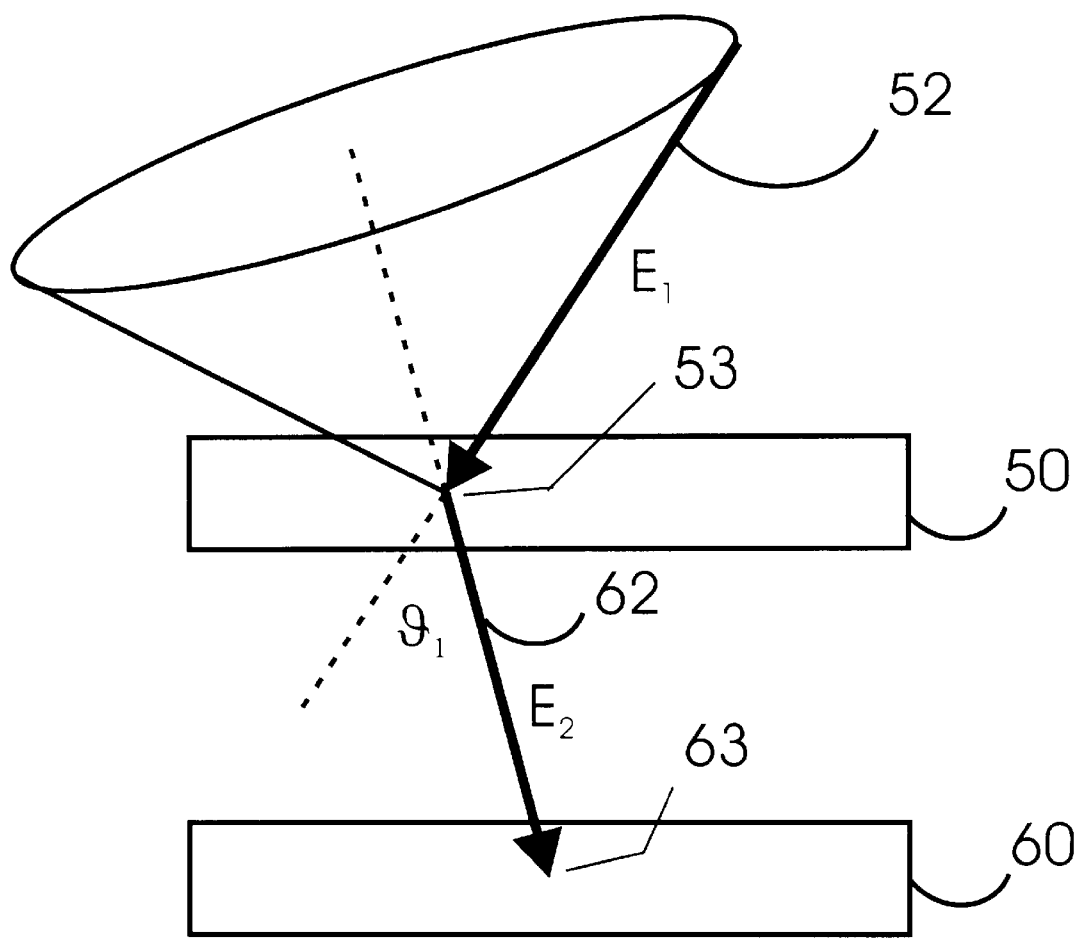
FIG. 1 is a diagram illustration of the Compton scatter process.

The invention makes use of the Compton scattering of gamma rays. Referring to FIG. 1, a gamma ray 52 is incident on a detector 50 in which the gamma ray undergoes a Compton scatter interaction at location 53. The detector 50 is such that both the location 53 and the energy loss to a Compton scattered electron can be precisely determined. The Compton scattered gamma ray 62 undergoes a photoelectric (full-energy) interaction at location 63 in a second detector 60 such that the location 63 and the energy loss at location 63 can be precisely determined. It is well known to those skilled in the art that the scatter angle $\theta_1$ is uniquely determined by the energy losses at locations 53 and 63 under the assumption that the initial momentum of the Compton scattered electron is zero. The angle of scattering is given by:

$$\cos\vartheta_1 = 1 - mc^2\left(\frac{1}{E_2} - \frac{1}{E_1}\right) \quad (1)$$

where $E_2$ is the energy of the scattered gamma ray (and the energy deposited at location 63) and $E_1$ is the energy of the incident gamma ray (and also the sum of the energy losses at locations 53 and 63).

Figure 2:
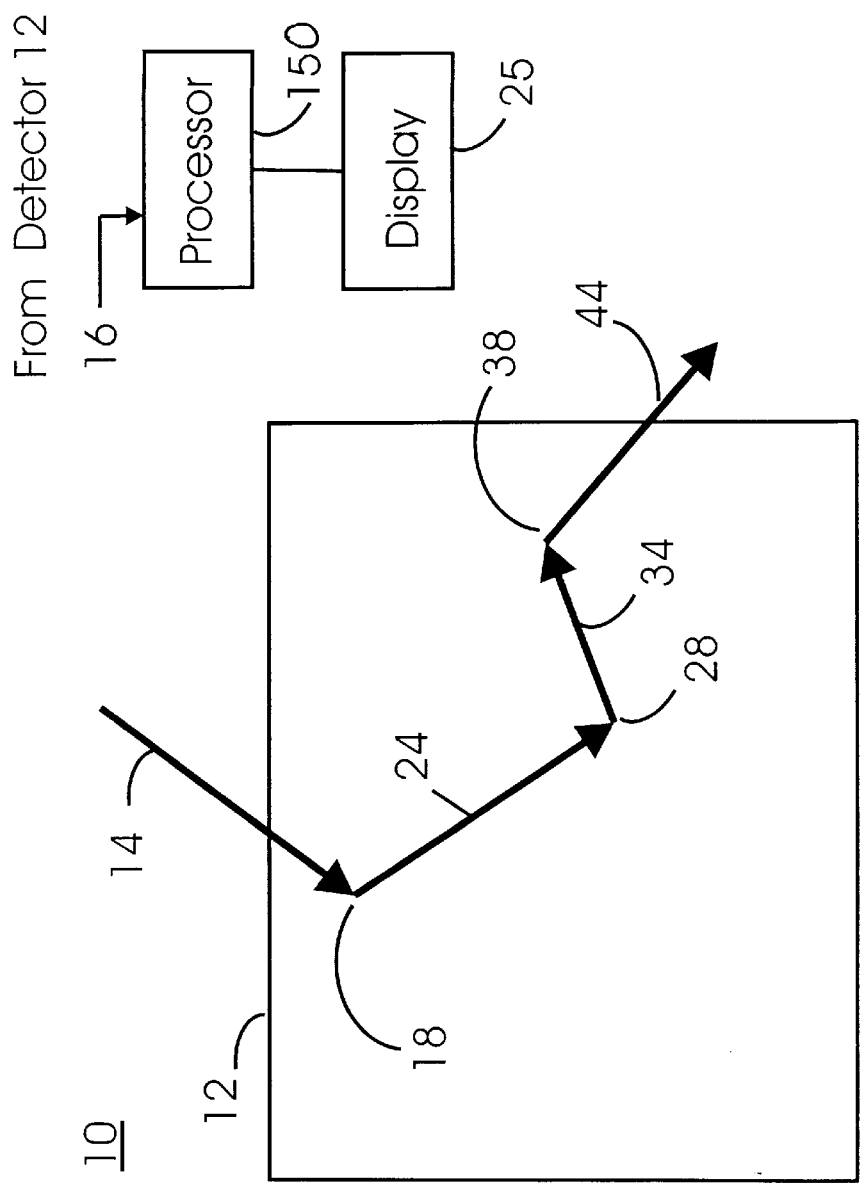
FIG. 2 is a diagram of an embodiment illustrating the use of a monolithic position-sensitive detector system according to the invention.

Referring now to FIG. 2, a gamma ray detection system 10 includes detector 12, which comprises a device capable of interacting with and scattering an incident gamma ray 14 while providing an output 16 to processor 15 from each scattering event as will be further explained below. Detector 12 may comprise a position-sensitive solid-state detector or a position-sensitive gaseous detector or a position-sensitive liquid-filled detector. The solid-state detector could be one of a number of solid state detector materials as are described further below.

Gamma ray 14 is scattered in detector 12 in a first Compton-scattering interaction at a first location 18. First Compton-scattered gamma ray 24 interacts in a second Compton-scattering event at a second location 28 to produce a second Compton-scattered gamma ray 34. Gamma ray 34 may interact in a third Compton-scattering event or may undergo a photoelectric interaction at a third location 38. In the event that gamma ray 34 interacts through a third scattering event at location 38, a third Compton-scattered gamma ray is produced which can exit the detector 12. The output data 16, i.e. the location and energy deposited from each scattering event in detector 12, is input to a processor 15. Processor 15 includes a program for calculating, based on the energy losses at locations 18 and 28 and the angle of scattering at location 28 determined from the locations 18, 28, and 38, the direction cone and energy of the incident gamma ray 14 as is described below. The processor outputs this data to display unit 25 which can display, among other information, the incident direction cone of each gamma ray, a two-dimensional map representing the gamma ray sources in the field, and the energy spectra of sources in selected regions in the map.

Figure 3:
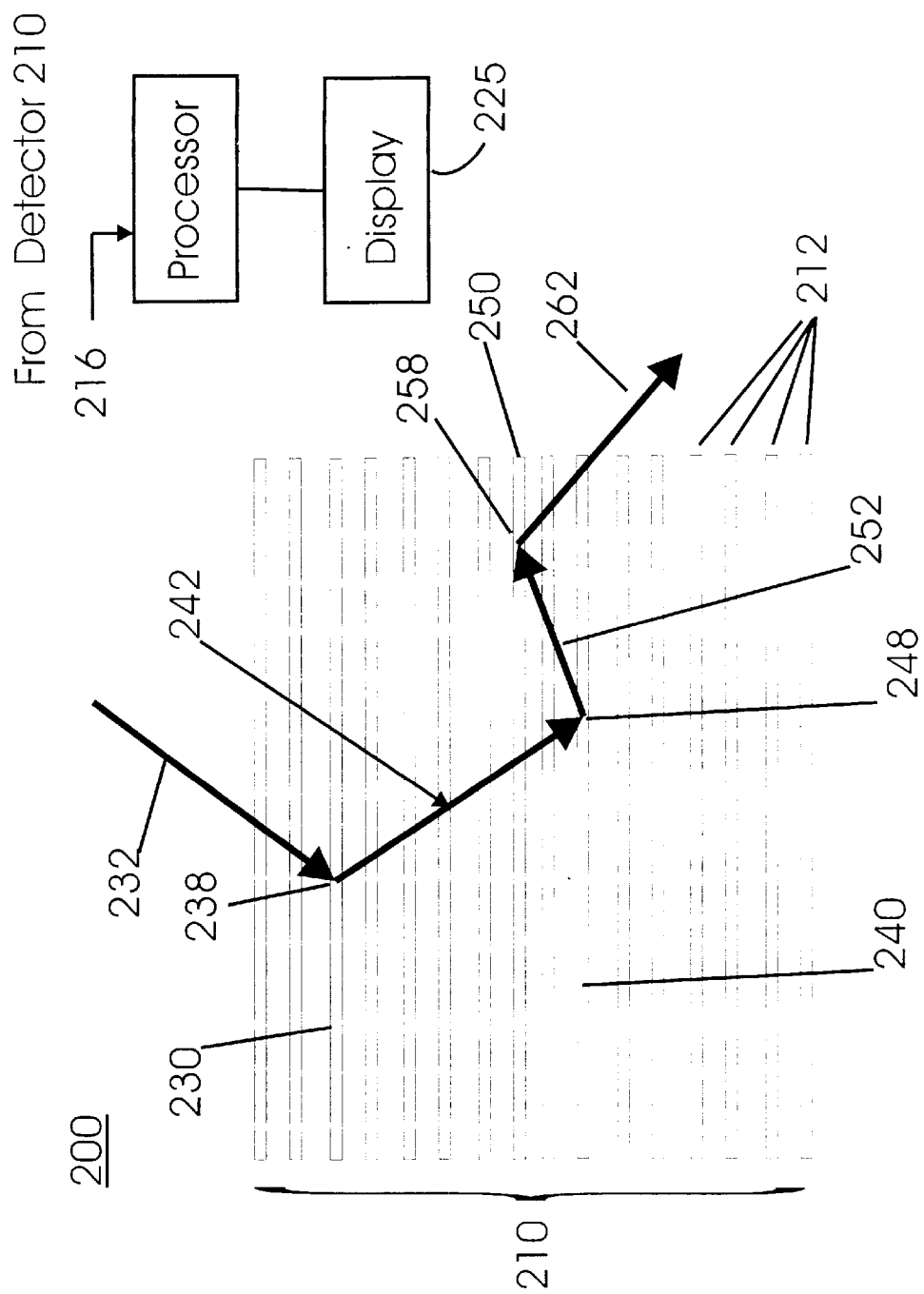
FIG. 3 is a cross sectional view of a Compton imaging instrument illustrating the use of arrays of position-sensitive solid-state detectors according to the invention.

Referring now to FIG. 3, in another embodiment of the invention, a gamma ray detection system 200 includes a detector array 210 that comprises a plurality of individual detector layers 212 each of which serves as a position-sensitive solid-state detector. Each layer 212 of array 210 comprises a material able to interact with an incoming gamma ray 232 by Compton scattering and by additional interaction mechanisms as are well known in the art. Useful materials for layers of 210 that exhibit good spectral resolution include germanium, silicon, CZT, CdTe, and GaAs, although other semi-conductor detectors known to provide acceptable spectral resolution are also within the scope of the invention. Silicon is a preferred material, as it combines highest relative probability of Compton scattering over a broad range of energies and can be used at near-room temperatures, unlike germanium-based prior art Compton detectors that are cryogenically cooled for acceptable performance.

Gamma ray 232 is Compton-scattered in a first interaction layer 230 at location 238. First Compton-scattered gamma ray 242 is then Compton-scattered in a second layer 240 at location 248. Second Compton-scattered gamma ray 252 is then Compton-scattered in a third layer 250 at location 258 or may be absorbed by a photoelectric interaction at location 258. If second Compton-scattered gamma ray 252 is Compton-scattered at location 258, then a third Compton scattered gamma ray 262 is produced that may exit the detector array 210. Since the detectors in each layer are position-sensitive, it is understood by those skilled in the art that two interactions may occur in the same layer. The output data 216 (the location and energy deposited from each interaction event) of detector array 210 is input to a processor 215. Processor 215 as in the case of processor 15 includes the program for calculating the direction cone and energy of the incident gamma ray 232 (described below). The processor outputs this data to display unit 225 which as before can display the incident direction cone of each gamma ray, a two-dimensional map, and the energy spectra of sources in selected regions in the map. For each interaction, the processor processes the electronic signals from the detector to determine the energy deposited at each interaction site and the x, y, and z coordinates for each energy loss.

Figure 4:
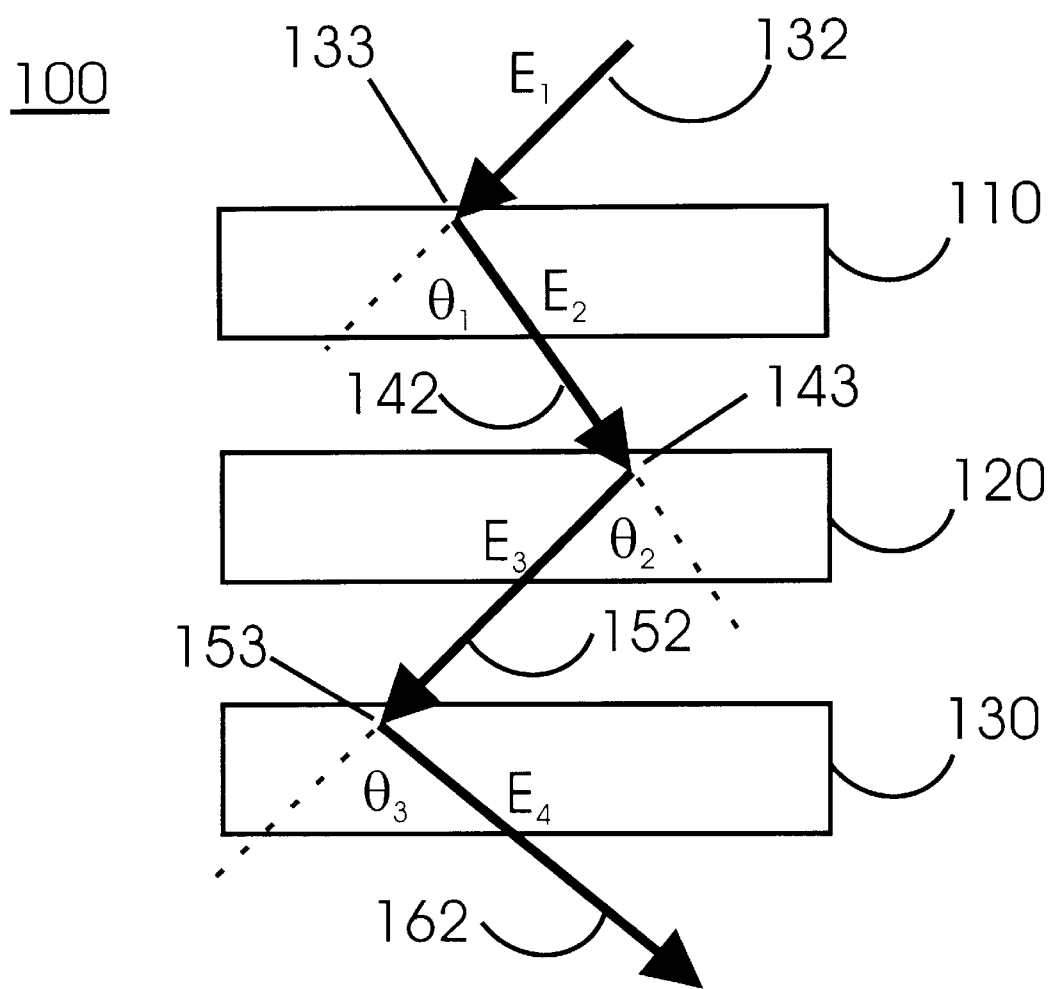
FIG. 4 illustrates the multiple Compton scattering process and detection scheme according to the invention.

We now show that the energy and direction angle of a gamma ray can be determined from only the partial energy loss at the first three interaction sites if the first two interactions are Compton scatters. Referring to FIG. 4, consider the two successive Compton scatter interactions followed by a third interaction. An initial gamma ray 132 with energy $E_1$, is incident on a detector array 100 which has good position resolution and good energy resolution. Gamma ray 132 interacts by a Compton scatter interaction in position-sensitive detector 110 at position 133. First Compton scattered gamma ray 142 leaves position 133 at an angle $\theta_1$ relative to the direction of the initial gamma ray 132, and interacts in position-sensitive detector 120 at position 143. Second Compton scattered gamma ray 152 leaves position 143 at an angle $\theta_2$ relative to the direction of the first Compton scattered gamma ray 142 and interacts in position-sensitive detector 130 at position 153. The interaction at position 153 can be a Compton scatter interaction producing third Compton scattered gamma ray 162 or a photoelectric interaction. Only the position in detector 130 is required. The energy losses (to the scattered electrons) at positions 133 and 143 are $L_1$, and $L_2$, respectively.

The Compton scattering formulae for the two interactions at positions 133 and 143 are:

$$\cos\vartheta_1 = 1 - mc^2\left(\frac{1}{E_2} - \frac{1}{E_1}\right) \quad (2)$$

$$\cos\vartheta_2 = 1 - mc^2\left(\frac{1}{E_3} - \frac{1}{E_2}\right) \quad (3)$$

where $mc^2$ is the rest mass of the electron, and the energies of the scattered electrons are:

$$L_1 = E_1 - E_2 \quad (4)$$

$$L_2 = E_2 - E_3 \quad (5)$$

Solving eq. (5) for $E_3$ and substituting into (3) yields an equation with $E_2$ as the only unknown, since $\theta_2$ is determined from the locations of the three interactions sites 133, 143 and 153. This quadratic equation can be solved for the energy $E_2$, and is given by:

$$E_2 = \frac{L_2}{2} + \frac{1}{2}\left[L_2^2 + \frac{4mc^2 L_2}{1 - \cos\vartheta_2}\right]^{\frac{1}{2}} \quad (6)$$

Therefore the incident gamma ray energy, $E_1$ is also determined from (4), and is:

$$E_1 = E_2 + L_1 = L_1 + \frac{L_2}{2} + \frac{1}{2}\left[L_2^2 + \frac{4mc^2 L_2}{1-\cos\vartheta_2}\right]^{\frac{1}{2}} \quad (7)$$

Now having $E_1$ and $E_2$, the scatter angle at the first interaction site and hence the direction cone for the initial gamma ray can be determined from equation (2). It is clear that determination of the correct energy and direction cone of the incident gamma ray requires that the correct sequence of interactions is known. This is accomplished through a procedure of testing the several possible interaction sequences and testing whether the Compton scatter interactions for each sequence is consistent with the kinematic relations for Compton scattering at each interaction site. In undertaking these tests, the probabilities for gamma rays of the inferred energies for each test sequence to travel from the nth interaction site to the (n+1)st interaction site through the required material can also be used to optimize the probability for obtaining the correct interaction sequence. This procedure is known to those skilled in the art and, for example, is described in U.S. Pat. No. 4,857,737, which is herein incorporated by reference.

The uncertainties in $E_1$ and $\theta_1$ can also be determined. The uncertainty in $E_1$, $dE_1$, is given by:

$$dE_1 = \left[\left(\frac{\partial E_1}{\partial L_1}dL_1\right)^2 + \left(\frac{\partial E}{\partial L_2}dL_2\right)^2 + \left(\frac{\partial E_1}{\partial \vartheta_2}d\vartheta_2\right)^2\right]^{\frac{1}{2}} \quad (8)$$

where $dL_1$ and $dL_2$ are the uncertainties in the energy depositions at interaction sites 133 and 143, and $d\theta_2$ is the uncertainty in the scattering angle at site 153 determined from the typical positional errors in the detector.

Figure 5:
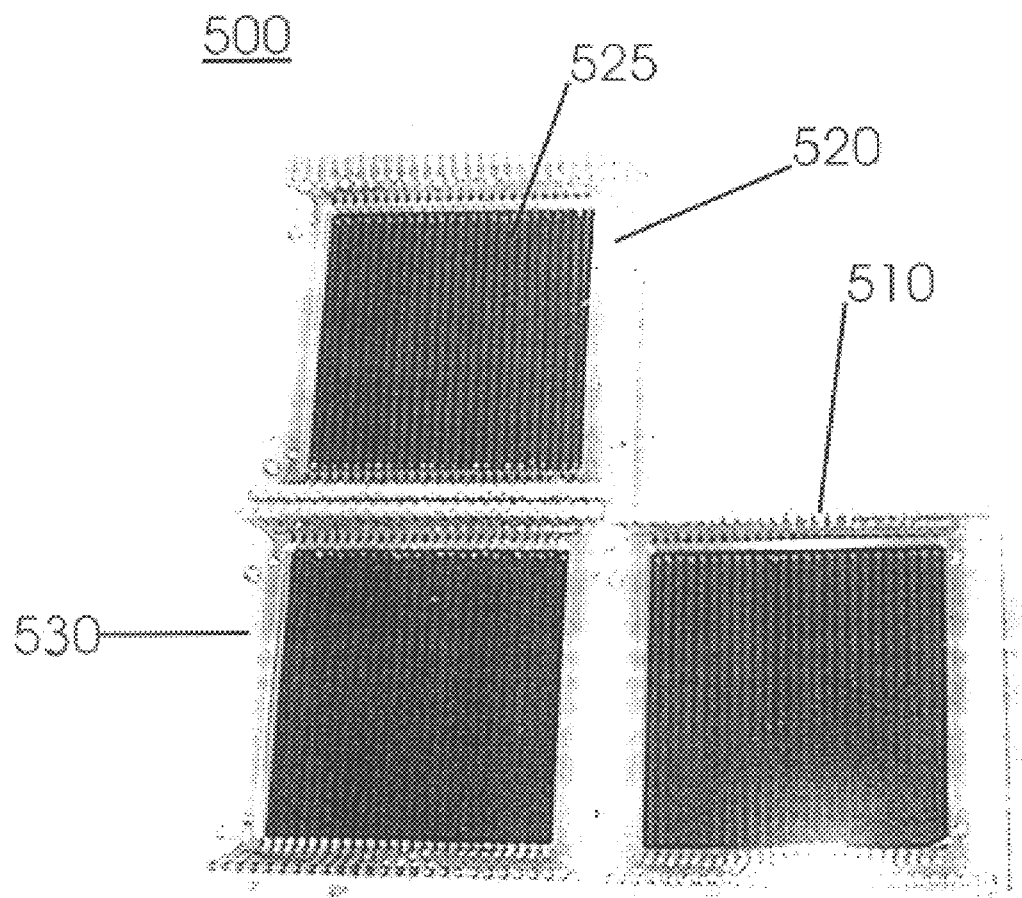
FIG. 5 shows an array of three position-sensitive solid-state strip detectors (germanium) applicable to the invention.

The position-sensitive device 200 illustrated in FIG. 3 indicates one possible implementation of a gamma ray detection system 210 that provides both excellent spectral resolution and excellent spatial resolution. Each of the several layers of the detector, exemplified by layers 230, 240 and 250 could consist of arrays of position-sensitive solid-state detectors. Referring to FIG. 5, an array 500 of three germanium strip detectors, 510, 520 and 530 is shown which are examples of the type of detectors that can be used to populate a detector device. Each of the strip detectors has an active area of 50 mm×50 mm and is 10 mm thick. The detectors have 25 orthogonal electrical contact strips on opposite sides of the planar faces as indicated by the strip 525. The pitch of the strips is 2 mm. One skilled in the art will know that when a gamma ray interacts by Compton scattering or photoelectric interaction in the active detector volume, electron-hole pairs are created. Under an applied electric field, the electrons drift toward one planar face and the holes drift toward the opposite face. The collection of the holes and electrons produce signals on a strip on each side of the detector. The location of the interaction in the planar dimension is determined by the intersection of the two strips that record the signals. For the devices shown, this location is determined to 2 mm accuracy in the x and y directions. Those skilled in the art will know that use of finer strip pitch enables position information in the x and y directions to be less than 1 mm.

Figure 6A:
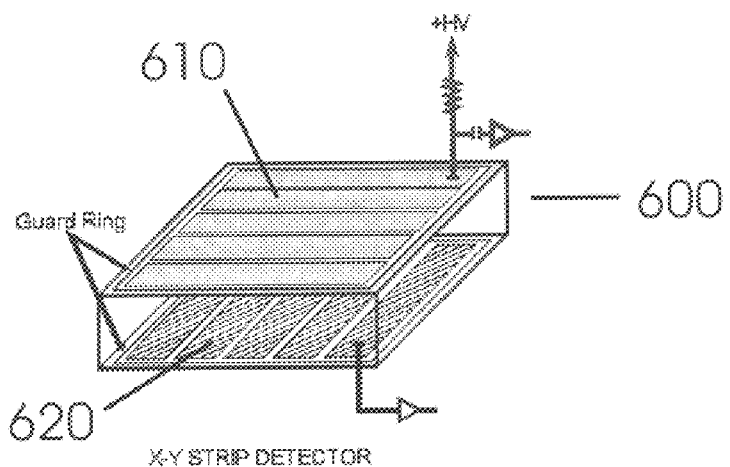
FIG. 6 is an illustration of using relative timing of anode and cathode signals in a germanium strip detector to achieve 3-dimensional positioning. The x-y position is derived from the orthogonal strips that receive the signals, and can determine positions to the strip pitch that may be less than 1 mm. The z-dimension is derived from the signal arrival times and can be determined to less that 0.5 mm.
Figure 6B:
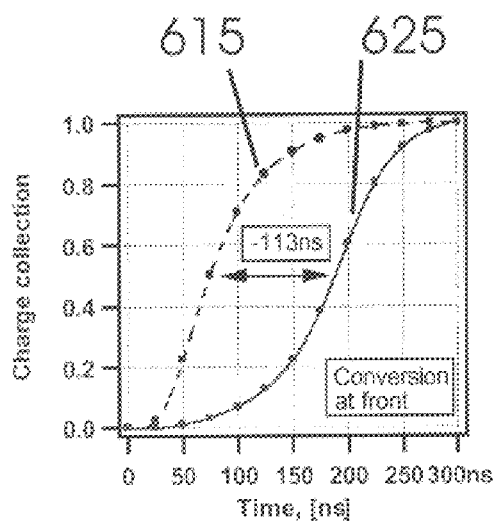
Figure 6C:
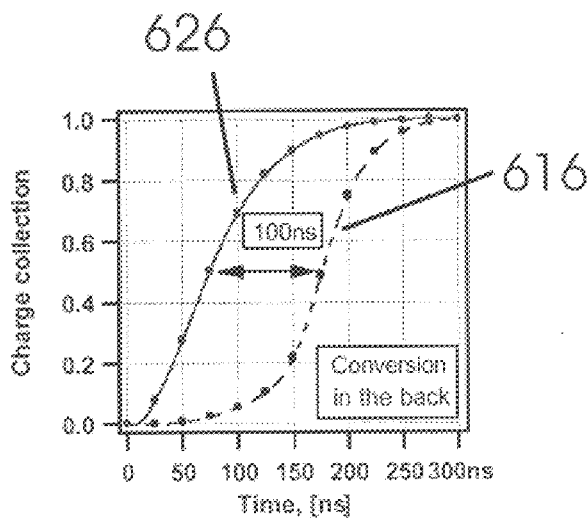

Excellent position resolution can also be achieved in the direction perpendicular to the x-y planar surfaces. This is achieved by measuring the relative arrival times of the electron and hole signals at the two strip surfaces. Referring to FIG. 6a, the orthogonal strips are shown schematically on opposite surfaces of a germanium strip detector. FIG. 6b shows the electron signal 615 acquired on strip 610 on the front face and the hole signal 625 acquired by the strip 620 on the back face of the detector for an interaction that occurs very near the front surface. It is understood by those skilled in the art that the rise time of the signal 615 precedes the rise of the signal 625 by about 100 nanoseconds. FIG. 6c shows the comparable signals 616 and 626 for an interaction that occurs near the back face of the detector. In this case the hole signal 626 arriving at strip 620 precedes the electron signal 616 arriving at strip 610 by about 100 nanoseconds. The total difference in the relative arrival times is about 200 nanoseconds. With an intrinsic resolving time of 10–20 nanoseconds, it is clear that the location of the interaction can be determined to less than 1 mm in the direction perpendicular to the strip faces of the detector. Combined with the x-y positions measured with the strip signals, the location of the interaction is measured to 1 mm or better in 3 dimensions. The uncertainty $d\theta_2$ is derived from the location uncertainties at the first three interaction sites.

Next, proceeding with equation (8) and evaluating the partial differential terms using equation (7), we obtain:

$$dE_1 = \left[dL_1^2 + \left(\frac{1}{2} + \frac{1}{4}\left[L_2^2 + \frac{4mc^2 L_2}{(1-\cos\vartheta_2)}\right]^{-\frac{1}{2}}\left[2L_2 + \frac{4mc^2}{(1-\cos\vartheta_2)}\right]\right)^2 dL_2^2 + \right. \quad (9)$$

$$\left. \left(\frac{\sin\vartheta_2}{4}\left[L_2^2 + \frac{4mc^2 L_2}{(1-\cos\vartheta_2)}\right]^{-\frac{1}{2}}\left[\frac{4mc^2 L_2}{(1-\cos\vartheta_2)^2}\right]\right)^2 d\vartheta_2^2\right]^{\frac{1}{2}}$$

The error in $\theta_1$ can also be determined. From (2) we have:

$$\cos\vartheta_1 = 1 - \frac{mc^2}{E_2} + \frac{mc^2}{E_1} = 1 - \frac{mc^2}{E_1 - L_1} + \frac{mc^2}{E_1} \quad (10)$$

$$d\cos\vartheta_1 = \left[\left(\frac{\partial\cos\vartheta_1}{\partial E_1}dE_1\right)^2 + \left(\frac{\partial\cos\vartheta_1}{\partial L_1}dL_1\right)^2\right]^{\frac{1}{2}} \text{ then:} \quad (11)$$

$$d\vartheta_1 = \frac{mc^2}{\sin\vartheta_1}\left[\left(\frac{1}{(E_1-L_1)^2} - \frac{1}{E_1^2}\right)^2 dE_1^2 + \frac{dL_1^2}{(E_1-L_1)^4}\right]^{\frac{1}{2}} \quad (12)$$

Figure 7:
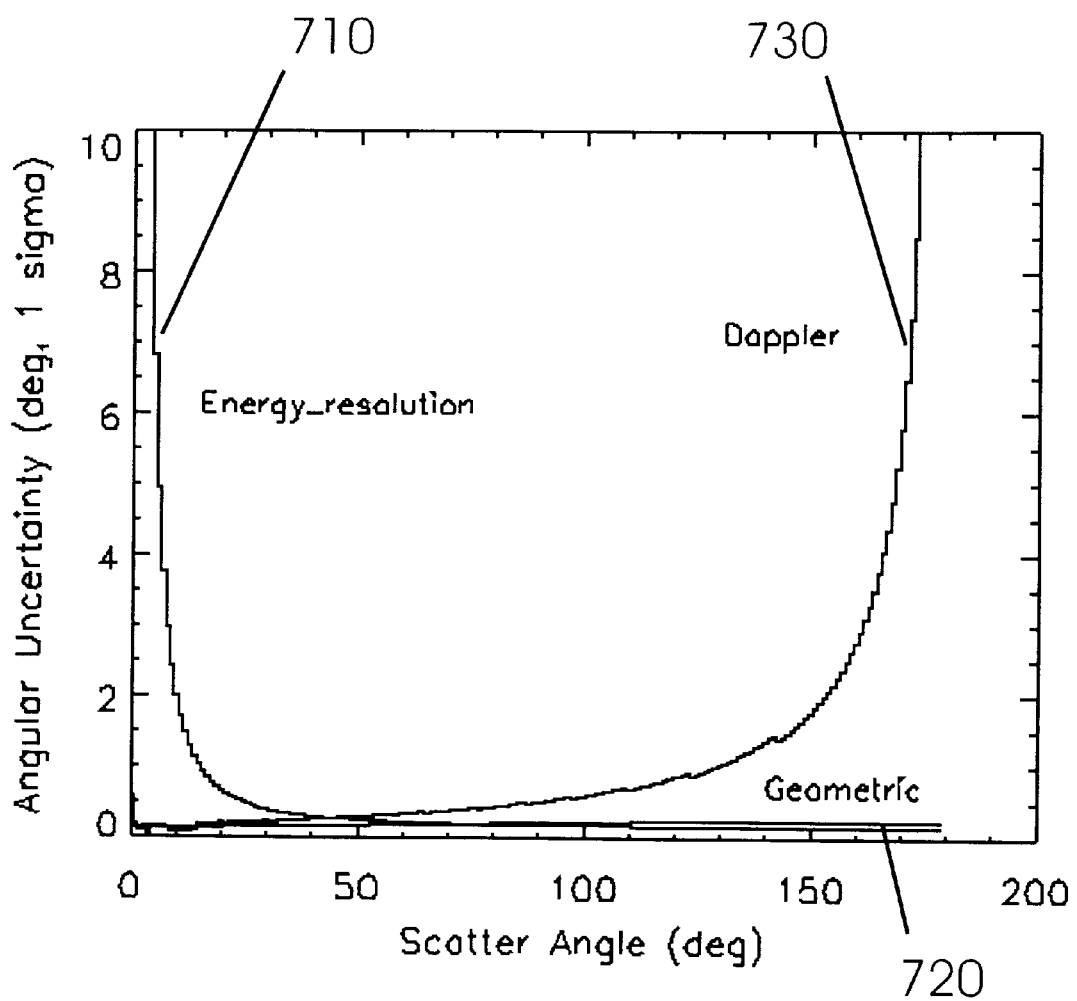
FIG. 7 illustrates the several components of the uncertainty in the Compton scatter angle including those due to energy resolution, position resolution, and Doppler broadening.

This uncertainty in the scattering angle at the first interaction site is due only to the uncertainty in the incident energy and the uncertainty in the energy loss in detector 110. In addition, there is an error associated with the uncertainties in the locations of the interactions at the three interaction sites. There is also an error associated with the initial momentum of the electron at position 133. This is assumed to be zero in the standard Compton formula derivation. Including the motion of the electron adds another uncertainty, commonly referred to as a Doppler broadening uncertainty and familiar to those skilled in the art. FIG. 7 shows the several components of the angular uncertainty as a function of Compton scatter angle for a 1 MeV incident gamma ray. These components include uncertainties due to the detector energy resolution 710, the detector position resolution 720 and the Doppler broadening 730.

The overall uncertainty in the direction of the incident gamma ray is given by the root-mean-square (RMS) sum of the three components 710, 720 and 730 due to the finite energy resolution of the detectors, the finite position resolution of the detectors and the Doppler broadening, respectively. This is given by:

$$d\theta_1^2(total) = d\theta_1^2(energy) + d\theta_1^2(geometric) + d\theta_1^2(Doppler) \quad (13)$$

FIG. 7 shows these uncertainties for the energy resolution 710, the geometric resolution 720 and the Doppler uncertainty 730 as a function of the Compton scattering angle for a 1 MeV incident gamma ray. In this case we have assumed a 2 keV FWHM energy resolution for the strip detectors, a 1 mm position resolution in three dimensions at each of the first three interaction sites, and a 15-cm mean-free-path between interactions (including the gaps between the layers of detectors). It is seen that for a broad range of scatter angles from about 20 degrees to 120 degrees, over which scatter angles the Compton cross section has a broad maximum, the total angular uncertainty is about 1 degree or less.

Figure 8:
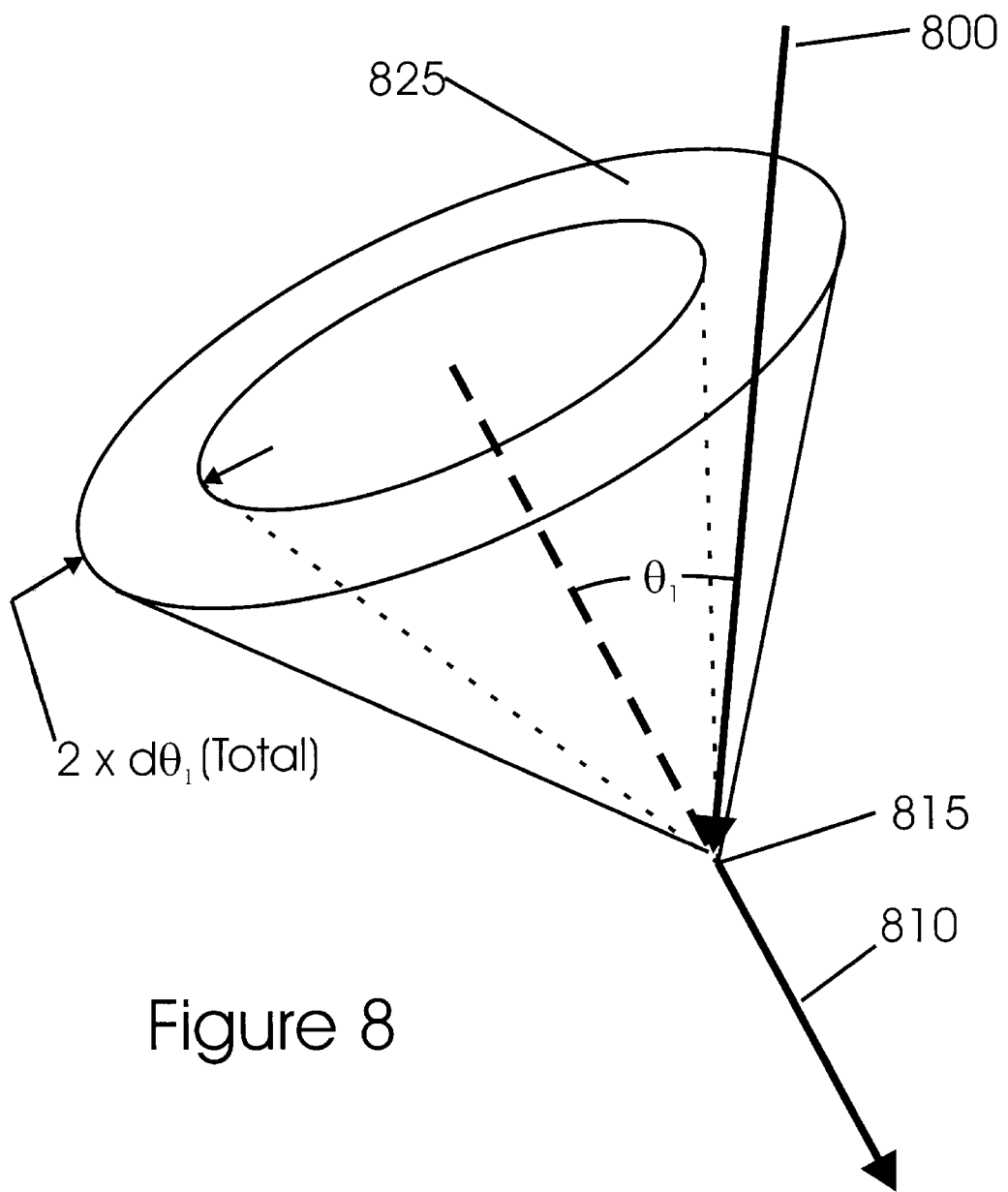
FIG. 8 shows a depiction of the direction cone illustrating factors leading to its calculation and determination, including the uncertainty in the Compton scatter angle.

The angular uncertainty in the direction of the incident gamma ray is indicated in FIG. 8. Incident gamma ray 800 Compton scatters at location 815 and Compton scattered gamma ray 810 leaves at an angle $\theta_1$ relative to the direction of incident gamma ray 800. The direction cone of the incident gamma rays is shown as 825, where the possible directions of the incident gamma ray is confined to an annular conical volume with a half opening angle of $\theta_1$ and an angular width of 2 times $d\theta_1$(total).

The excellent energy and spatial resolution of the detector enables the analysis of the several energy losses associated with an incident gamma ray (nearly coincident in time) to determine the sequence of interactions that are consistent with the energy and momentum Compton scattering laws at the first two interaction sites. This provides a unique determination of the direction cone and energy of the incident gamma ray, without necessitating the full absorption-based measurement and calculation from the incident gamma ray; however, it should also be understood that such a full absorption event is also accurately recorded, i.e. the incident gamma ray direction cone and energy accurately determined according to the technique elaborated on above, by the device and method of the invention.

Furthermore, background events, which are internal to the instrument or come from directions other than the field-of-view, are rejected with high efficiency. This is particularly important for gamma ray devices that operate in a high radiation environment such as those used in space. Take as an example a silicon detector array operating in space. A significant limitation on sensitivity and capability is imposed by the radiation produced by the interaction of cosmic ray and trapped particles in the Earth's high-energy radiation belts with the materials in the detector system and structure. Among the radioactive nuclei produced in abundance are for example, $^{22}$Na and $^{24}$Na which decay with the emission of gamma rays with characteristic energies (511 keV and 1275 keV for $^{22}$Na and 1369 keV and 2754 keV for $^{24}$Na). The techniques of this subject patent will prove useful to eliminate much of this background as follows. When a radioactive nuclide is produce and subsequently decays, the gamma ray will typically interact in the detector through several Compton interactions with escape of a Compton scattered gamma ray possible or likely. For those events that interact at least three times the several possible interaction sequences can be investigated to determine the likely energy and direction cone of the initial gamma ray. If this is consistent with the known gamma ray emission line energies of abundant spallation products and/or consistent with the direction of a coincident particle emitted during the decay, this event can be rejected by including the programming or algorithm run on processor 16 or 216 to discriminate out the selected detection event based on the positon and energy calculation matching or closely matching one or more of the predetermined values or parameters. It is evident that the ability to achieve this internal background rejection is greatly enhanced with detectors that provide both excellent energy and position resolution.

Obviously many modifications and variations of the present invention are possible in the light of the above teachings. It is therefore to be understood that the scope of the invention should be determined by referring to the following appended claims.

We claim:

1. A device for determining the photon energy $E_1$ and direction cone angle of incident gamma ray with two Compton scattering interactions and one subsequent interaction, comprising:

a first radiation detector for receiving an incident gamma ray having an unknown photon energy $E_1$ and an unknown direction, for scattering a photon energy $E_2$ in a first Compton scattering interaction at a first scatter angle $\theta_1$, and for providing a first output corresponding to the first Compton scattering interaction;

a second radiation detector for receiving photon energy $E_2$ and scattering some photon energy $E_3$ in a second Compton scattering interaction at a second scatter angle $\theta_2$, and for providing a second output corresponding to the second Compton scattering interaction;

a third radiation detector for receiving photon energy $E_3$, and interacting with photon energy $E_3$ in a third interaction, and for providing a third output corresponding to the third interaction; and a processor for receiving and processing said first, second, and third outputs and for calculating said photon energy $E_1$ and direction cone angle of said incident gamma ray based on said outputs, said first and second radiation detectors being sensitive to the position and energy of incident gamma ray and said third radiation detector being sensitive to at least the position of incident gamma ray, and wherein said calculating of said photon energy $E_1$ and direction cone angle of said incident gamma ray does not require absorption and measurement of the entire or substantially all the energy $E_1$ in said device.

2. A device as in claim 1, wherein said processor includes an algorithm for calculating the respective energy losses $L_1$ and $L_2$ in said first and second radiation detectors, from said respective first and second scattering interactions.

3. A device as in claim 2, wherein said algorithm calculates a) said photon energy $E_1$ as a function of said energy loss $L_1$ of said first detector and of said energy $E_2$, and b) said direction cone angle of said incident radiation as a function of said first scattering angle $\theta_1$, said first scattering angle $\theta_1$ being a cosine function of said energies $E_1$ and $E_2$.

4. A device as in claim 3, wherein said algorithm calculates said photon energy $E_1$ according to the equation $$E_1 = L_1 + \frac{L_1}{2} + \frac{1}{2}\left[L_2^2 + \frac{4mc^2 L_2}{1 - \cos\theta_2}\right]^{\frac{1}{2}},$$

wherein $mc^2$ is the rest mass of an electron, and calculates said first scattering angle according to the equation $$\cos\phi_1 = 1 - \frac{mc^2}{E_1 - L_1} + \frac{mc^2}{E_1}.$$

5. A device as in claim 4, wherein said algorithm further calculates the uncertainty in the photon energy $E_1$ as a function of the uncertainties in the energy depositions at said first and said second detectors, said gamma ray energies $E_1$ and $E_2$, said direction cone angles $\theta_1$ and $\theta_2$, and said energy losses $L_1$ and $L_2$ in said first and second radiation detectors due to Compton scattering.

6. A device as in claim 5, wherein said algorithm calculates said uncertainty in the photon energy $E_1$ according to $$dE_1 = \left[ \left[ dL_1^2 + \left( \frac{1}{2} + \frac{1}{4} \left[ L_2^2 + \frac{4mc^2}{(1-\cos\theta_2)} \right]^{\frac{1}{2}} \left[ 2L_2 + \frac{4mc^2}{(1-\cos\theta_2)} \right] \right)^2 dL_2^2 + \right. \right.$$
$$\left. \left. \left( \frac{\sin\theta_2}{4} \left[ L_2^2 + \frac{4mc^2 L_2}{(1-\cos\theta_2)} \right]^{\frac{1}{2}} \left[ \frac{4mc^2 L_2}{(1-\cos\theta_2)^2} \right] \right)^2 d\theta_2^2 \right] \right]^{\frac{1}{2}}.$$

7. A device as in claim 4, wherein said algorithm further calculates the uncertainty in said first scatter angle $\theta_1$ according to $$d\theta_1 = \frac{mc^2}{\sin\theta_1} \left[ \left( \frac{1}{(E_1-L_1)} - \frac{1}{E_1^2} \right)^2 dE_1^2 + \frac{dL_1^2}{(E_1-L_1)^4} \right]^{1/2},$$

wherein $mc^2$ is the rest mass of an electron.

8. A device as in claim 1, wherein said radiation detectors are high purity gas detectors.

9. A device as in claim 1, wherein said radiation detectors are solid state radiation detectors.

10. A device as in claim 9, wherein said solid state radiation detectors are orthogonal strip detectors, pixel detectors, drift detectors, or combinations thereof.

11. A device as in claim 10, wherein said solid state radiation detectors are germanium, silicon, Cadmium Zinc Telluride, Cadmium Telluride, or Gallium Arsenide, or combinations thereof.

12. A device as in claim 10, wherein said solid state radiation detectors are arrays of planar detectors comprising orthogonal strips on opposite sides of two faces of said planar detectors.

13. A device as in claim 1, wherein said processor is programmed to reject a selected detection event.

14. A device for determining the direction cone angle of incident gamma ray with one Compton scattering interaction and a subsequent interaction if the photon energy E1 of the incident gamma ray is known, comprising:

a first radiation detector for receiving gamma ray having photon energy $E_1$ and unknown direction cone angle, said first radiation detector being adapted to scatter some photon energy $E_2$ according to the Compton scatter effect at a first scatter angle $\theta_1$, and a second radiation detector positioned to receive photon energy $E_2$, wherein said first radiation detector is sensitive to the position and energy of the incident gamma ray and said second radiation detector is sensitive to the position of the Compton scattered gamma ray, or said first radiation detector is sensitive to the position of the incident gamma ray and said second radiation detector is sensitive to the position and absorbs the full energy of the Compton-scatterd gamma ray, and wherein a calulation of said photon energy $E_1$ and direction cone angle of said incident gamma ray does not require the absorption and measurement of the entire or substantially all the energy $E_1$ in said device.

15. A device as in claim 14, further comprising means for measuring the energy loss $L_1$ in said first radiation detector due to Compton scattering.

16. A device as in claim 15, further comprising a processor programmed to calculate said first scatter angle as a function of said photon energy $E_1$ and loss $L_1$ in said first radiation detector due to Compton scattering.

17. A device as in claim 16, wherein said processor is programmed to calculate said first scatter angle $\theta_1$ according to $$\cos\theta_1 = 1 - \frac{mc^2}{E_1 - L_1} + \frac{mc^2}{E_1},$$

wherein $mc^2$ is the rest mass of an electron.

18. A device as in claim 17, wherein said processor is further programmed to calculate said first scatter angle $\theta_1$ according to $$d\theta_1 = \frac{mc^2}{\sin\theta_1} \left[ \left( \frac{1}{(E_1-L_1)} - \frac{1}{E_1^2} \right)^2 dE_1^2 + \frac{dL_1^2}{(E_1-L_1)^4} \right]^{1/2},$$

wherein $mc^2$ is the rest mass of an electron.

19. A device as in claim 14, wherein said radiation detectors are high purity gas detectors.

20. A device as in claim 14, wherein said radiation detectors are solid state radiation detectors.

21. A device as in claim 20, wherein said solid state radiation detectors are orthogonal strip detectors, pixel detectors, drift detectors, or combinations thereof.

22. A device as in claim 20, wherein said solid state radiation detectors are germanium, silicon, Cadmium Zinc Telluride, Cadmium Telluride, or Gallium Arsenide, or combinations thereof.

23. A device as in claim 20, wherein said solid state radiation detectors are arrays of planar detectors comprising orthogonal strips on opposite sides of two faces of said planar detectors.

24. A device as in claim 14, wherein said processor is programmed to reject a selected detection event.

25. A device for determining the photon energy $E_1$ and direction cone angle of incident gamma ray with two Compton scattering interactions and one subsequent interaction, comprising:

a detector for receiving an incident gamma ray having an unknown photon energy $E_1$ and an unknown direction, and for (a) scattering a photon energy $E_2$ in a first Compton scattering interaction at a first scatter angle $\theta_1$, and for providing a first output corresponding to the first Compton scattering interaction, (b) receiving photon energy $E_2$ and scattering some photon energy $E_3$ in a second Compton scattering interaction at a second scatter angle $\theta_2$, and for providing a second output corresponding to the second Compton scattering interaction, and (c) receiving photon energy $E_3$, and interacting with photon energy $E_3$ in a third interaction, and for providing a third output corresponding to the third interaction; and a processor for receiving and processing said first, second, and third outputs and for calculating said photon energy $E_1$ and direction cone angle of said incident gamma ray based on said outputs, and wherein said radiation detector is sensitive to the position and energy of incident gamma ray, and wherein said calculating of said photon energy $E_1$ and direction cone angle of said incident gamma ray does not require absorption and measurement of the entire or substantially all the energy $E_1$ in said device.

26. A device as in claim 25, wherein said processor is programmed to reject a selected detection event.

27. A method for determining the photon energy $E_1$ and direction cone angle of incident gamma ray with two Compton scattering interactions and one subsequent interaction, comprising the steps of:

receiving an incident gamma ray having an unknown photon energy $E_1$ and an unknown direction cone angle, for scattering a photon energy $E_2$ in a first Compton scattering interaction at a first scatter angle $\theta_1$, and providing a first output corresponding to the first Compton scattering interaction;

receiving photon energy $E_2$ and scattering some photon energy $E_3$ in a second Compton scattering interaction at a second scatter angle $\theta_2$, and providing a second output corresponding to the second Compton scattering interaction;

receiving photon energy $E_3$, and interacting with photon energy $E_3$ in a third interaction, and providing a third output corresponding to the third interaction; and processing said first, second, and third outputs and calculating said photon energy $E_1$ and direction cone angle of said incident gamma ray based on said outputs, wherein said calculating of said photon energy $E_1$ and direction cone angle of said incident gamma ray does not require absorption and measurement of the entire or substantially all the energy $E_1$.

\* \* \* \* \*